United States Patent

Kassing et al.

[11] Patent Number: 5,516,669
[45] Date of Patent: May 14, 1996

[54] TRANSPOSON CONSISTING OF A FRAGMENT OF THE R PLASMID PCXM82B, TEST VECTORS CONTAINING THIS TRANSPOSON, AND METHODS OF MUTAGENESIS

[75] Inventors: Friedrich Kassing, Gutersloh; Andreas Schäfer, Bielefeld; Jörn Kalinowski, Bielefeld; Alfred Puhler, Bielefeld, all of Germany

[73] Assignee: Degussa Aktiengesellschaft, Frankfurt am Main, Germany

[21] Appl. No.: 181,164

[22] Filed: Jan. 13, 1994

Related U.S. Application Data

[63] Continuation of Ser. No. 664,614, Mar. 4, 1991, abandoned.

[30] Foreign Application Priority Data

Mar. 3, 1990 [DE] Germany .................. 40 06 637.1

[51] Int. Cl.$^6$ .................. C12N 1/21; C12N 15/52; C12N 15/63; C12N 15/77
[52] U.S. Cl. .................. 435/172.3; 435/252.32; 435/320.1; 536/23.2
[58] Field of Search .................. 435/172.3, 252.3, 435/252.31, 252.32, 320.1; 536/23.2

[56] References Cited

PUBLICATIONS

Kono et al. (Mar. 1983), Antimicrob. Agents Chemother., vol. 23(3), pp. 506–508.
Serwold–Davis et al. (Nov. 1988), FEMS Mirobiol. Lett., vol. 56, pp. 7–14.
Trieu–Cuot et al. (Dec. 1987), FEMS Microbiol. Lett., vol. 48, pp. 289–294.
Vandeyar et al., (Aug. 1986), J. Bacteriol., vol. 167(2), pp. 530–534.

Primary Examiner—Mindy Fleisher
Assistant Examiner—Philip W. Carter
Attorney, Agent, or Firm—Cushman, Darby & Cushman

[57] ABSTRACT

The invention relates to a transposon consisting of a fragment of the R plasmid pCxM82B from *Corynebacterium xerosis* DSM 5021, to mobilizable, non-self-transferrable vectors which contain this transposon, and to methods for the mutagenesis of gram-positive bacteria by means of the transfer of these vectors and the generation of auxotrophic mutants.

13 Claims, 3 Drawing Sheets

TRANSPOSON CONSISTING OF A FRAGMENT OF THE R PLASMID PCXM82B, TEST VECTORS CONTAINING THIS TRANSPOSON, AND METHODS OF MUTAGENESIS

This is a continuation of application Ser. No. 07/664,614, filed on Mar. 4, 1991, which was abandoned upon the filing hereof.

BACKGROUND OF THE INVENTION

1. Field of the Invention

The present invention relates, in general, to a transposon. In particular, the present invention relates to a transposon consisting of a segment of the resistance (R) plasmid pCxM82B, test vectors containing this transposon, and methods of mutagenesis.

2. Background Information

Transposons contain a DNA sequence encoding a protein which makes it possible for the transposon to integrate non-specifically into the DNA of a chromosome or of a plasmid by means of illegitimate recombination. In addition, a transposon comprises a selectable marker (e.g. an antibiotic resistance gene). The presence of a selectable marker within the transposon aids in the identification and selection of cells containing this transposon. Therefore, it is possible to directly identify transposon-tagged integration mutants and determine the localization of the particular transposon-tagged gene in the genome. The isolation of a restriction fragment containing the particular gene and the inserted transposon can then take place in accordance with methods known in the art.

In contrast to transposon mutagenesis, traditional methods of mutagenesis (hydroxylamine mutagenesis and NTG mutagenesis) often negatively influence the vitality of the organism. Another problem associated with using traditional methods of mutagenesis to study genes is the inability to rapidly localize the mutated gene.

The technique of transposon mutagenesis is already being used successfully in gram-positive and in gram-negative bacteria. Note here by way of example the transposons Tn10 (9.3 kb, tetracycline resistance (Tc')) of plasmid R100 (Kleckner et al. (1981) Ann. Rev. Genet. 15, 341ff) and Tn5 (5.7 kb, kanamycin resistance (Km')) from the plasmid JR67 (Berg et al. (1975) Proc. Natl. Acad. Sci. USA 72, 3628ff), both from gram-negative bacteria, and the transposons Tn917 (5.1 Kb, Em') from the plasmid pAD2 (Tomich et al. (1980) J. Bact. 141, 1366ff) and Tn916 (15 kb, Tc') from the chromosome of *Streptococcus faecalis* DS16, both from gram-positive bacteria.

The transposon Tn917 was used successfully in bacillus ssp as well as in other gram-positive and gram-negative organisms (Kuramitsu and Casadaban (1986) J. Bact. 167, 711f) for generating auxotrophic cells mutant in amino-acid metabolism or in energy metabolism (Perkins and Youngman (1984) Plasmid 12, 119ff; Vandeyar and Zahler (1986) J. Bact. 167, 530ff; Mc Laughlin and Hughes (1989) J. Gen. Microbiol. 135, 2329).

In addition, transposons are presently being used for genome mapping, for the mobilization of replicons, for the generation of operon fusions and for the induction of genes (Simon et al. (1989) Biotechnology 1, Methods in Enzymology 118, 641–659).

Unfortunately, the known transposon-mutagenesis systems are not suitable for the mutating and genetic engineering of coryneform bacteria, especially those coryneform bacteria which produce and excrete amino acids.

SUMMARY OF THE INVENTION

It is a general object of this invention to provide a transposon.

It is a specific object of this invention to provide a transposon consisting of a DNA segment of the R plasmid pCxM82B. This plasmid has been deposited in the German Collection of Microorganisms, Mascheroder Weg 16, D-38124 Braunschweig, on Feb. 3, 1990, and has been given the accession number DSM 5021.

It is another object of the invention to provide a mobilizable, non-self-transferrable vector (test vector).

It is a further object of the invention to provide a method for the mutagenesis of a gram-positive bacterium.

It is a further object of the invention to provide a gram-positive bacterium containing a mobilizable, non-self-transferrable vector (test vector).

Further objects and advantages of the present invention will be clear from the description that follows.

In one embodiment, the present invention relates to a transposon consisting of a DNA segment of the R plasmid pCxM82B.

In another embodiment, the present invention relates to a mobilizable, non-self-transferrable vector (test vector) comprising:

a) a mobilizable, non-self-transferrable *Escherichia coli* (*E. coli*) vector, and b) a transposon consisting of a DNA segment of the R plasmid pCxM82B.

In a further embodiment, the present invention relates to a method for the mutagenesis of a gram-positive bacterium comprising introducing a transposon consisting of a DNA segment of the R plasmid pCxM82B with the aid of a carrier plasmid into the bacterium.

In yet another embodiment, the present invention relates to a method for the mutagenesis of a gram-positive bacterium comprising conjugative transfer of mobilizable vectors from *E. coli* mobilizer strains wherein the vectors contain a transposon consisting of a DNA segment of the R plasmid pCxM82B.

In a further embodiment, the present invention relates to a gram-positive bacterium wherein the bacterium is transformed with a mobilizable, non-self-transferrable vector (test vector) containing a transposon consisting of a DNA segment of the R plasmid pCxM82B.

a) the DNA segment essential for the integration is located between the coordinates 30.4–44.8 kb on the R plasmid, b) the DNA segment limited at coordinate 30.4 kb by a SalI cleavage site and at coordinate 44.8 kb by a HindIII cleavage site and c) the DNA segment coding for a tetracycline resistance and erythromycin resistance.

Figure 2A:
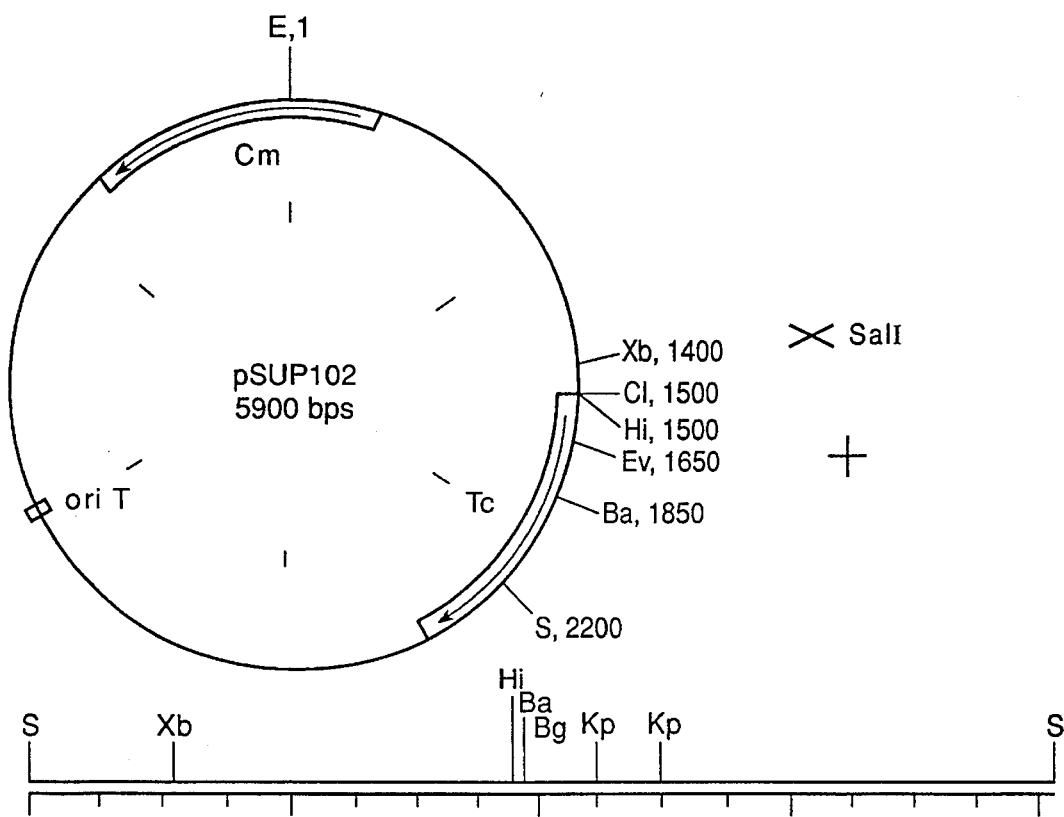

FIGS. 2a and b. Plasmid pSUP102 and pK2 is shown. Abbreviations used in the figures include: Ba, BamHI; Bg, BglII; Cl, ClaI; E, EcoRI; EV, EcoRV; Hi, HindIII; Kp, KpnI; Ns, NsiI; P, PstI; S, SalI; Xb, XbaI; Hp, HpaI.

Figure 3A:
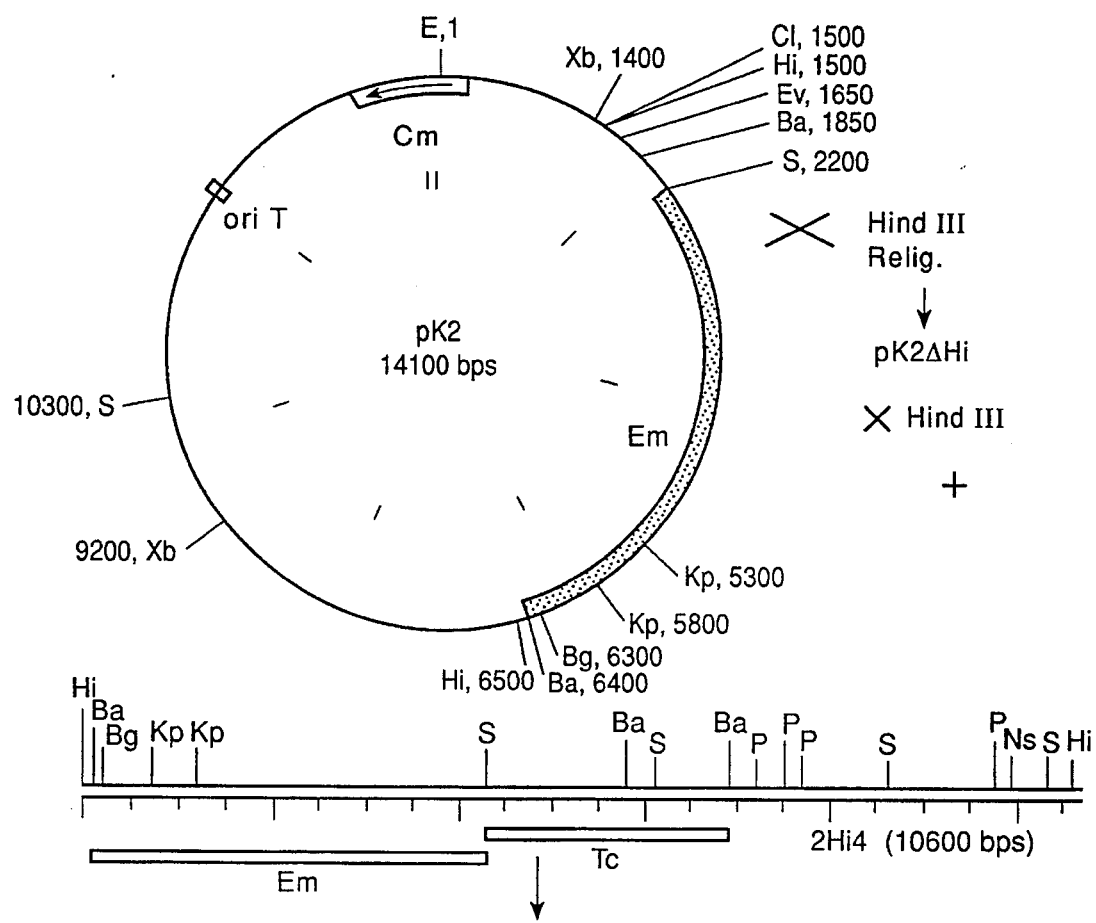

FIGS. 3a and b. Plasmid pK1 and pK2 are shown. Abbreviations used in the figures include: Ba, BamHI; Bg, BglII; Cl, ClaI; E, EcoRI; Ev, EcoRV; Hi, HindIII; Kp, KpnI; Ns, NsiI; P, PstI; S, SalI; Xb, XbaI; Hp, HpaI. A deposit of plasmid pK1 has been made in the German Collection of Microorganisms, Mascheroder Weg 16, D-38124 Braunschweig, on Jun. 6, 1995, and has been given the accession number DSM 10019.

DETAILED DESCRIPTION OF THE INVENTION

The present invention relates to transposon consisting of a DNA segment of the R plasmid pCxM82B wherein the DNA segment comprises:

(a) a segment of DNA necessary for integration, (b) a segment of DNA coding for tetracycline resistance, and (c) a segment of DNA coding for erythromycin resistance. In one preferred embodiment, the transposon comprises an approximately 14.4 kb DNA segment delimited by a SalI cleavage site (coordinate 30.4 kb) and a HindIII cleavage site (coordinate 44.8 kb) of pCxM82B set forth in FIG. 1.

It was found that a certain segment of the R plasmid pCxM82B from *Corynebacterium xerosis* DSM 5021 exhibits transposon activity. The R plasmid is deposited in the German Collection of Microorganisms according to the Budapest Convention in *Corynebacterium xerosis* DSM 5021 and is described in European patent application No. 89 120 459.6 (corresponding to German patent application P 38 41 454.6).

The transposon activity is displayed as well in gram-positive bacteria, especially in coryneform bacteria such as e.g. *Corynebacterium (C.) glutamicus, C. xerosis, C. acetoacidophilum, C. herculis, C. lilium, C. melassecola. Brevibacterium (B.) flavum, B. thiogenitalis, B. lactofermentum, B. roseum, B. saccharoliticum*, especially *Brevibacterium lactofermentum* DSM 20412, *Corynebacterium callunae* DSM 20147, *Corynebacterium herculis* DSM 20301, *Brevibacterium flavum* DSM 20411, *Arthrobacter albidus* DSM 20128, with those being preferred which produce and excrete amino acids.

In another embodiment the present invention relates to a mobilizable, non-self-transferrable vector (test vector) comprising:

a) a mobilizable, non-self-transferrable *E. Coli* vector comprising a DNA segment containing a replicon functional in *E. coli* and a second DNA segment containing DNA segments coding for the mobilization and transfer functions (Mob site and ori T), and b) the transposon described above. In one preferred embodiment the mobilizable, non-self-transferrable *E. coli* vector contains a 1.9 kb DNA fragment (mob site) of the plasmid RP4. In another preferred embodiment, the mobilizable, non-self-transferrable *E. coli* vector is pSUP101, pSUP102, pSUP201, pSUP202, pSUP203, pSUP205, pSUP301, or pSUP401. In a further preferred embodiment, the mobilizable, non-self-transferrable vector (test vector) is pK1 set forth in FIG. 3.

The concept *E. coli* vectors includes in a general fashion all plasmids which replicate independently only in *E. coli* strains and which have proven to be useful according to the state of the art for genetic engineering applications. Examples of such *E. coli* vectors are pMB9, pBR322, pBR325, pKB111, pUC8, pUC9, pACyCl84, pACYCl177, or pSC101. These and other vectors which replicate only in bacteria strains of the *E. coli* group are modified by means of insertion of the mob site of a plasmid with a broad host range in gram-negative bacteria. Suitable mobilizer strains are modified *E. coli* strains which contain a plasmid integrated into the chromosome or present in a free manner which is capable of making available the functions necessary for mobilization.

Strains are suitable in particular in whose chromosome an RP4 derivative is integrated whose transfer function acts in trans on the mob site of the above-named vectors.

Table 1

Suitable vectors and *E. coli* mobilizer strains are known from U.S. Pat. No. 4,626,504 and are deposited in the Northern Regional Research Center:

| Strains | NRRL deposit number |
| --- | --- |
| *E. coli* CSH52/pSUP101 | B - 15484 |
| *E. coli* CSH52/pSUP201 | B - 15487 |
| *E. coli* CSH52/pSUP202 | B - 15488 |
| *E. coli* CSH52/pSUP203 | B - 15489 |
| *E. coli* CSH52/pSUP301 | B - 15492 |
| *E. coli* CSH52/pSUP401 | B - 15494 |
| *E. coli* SM;10 | B - 15481 |
| *E. coli* S68-7 | B - 15482 |
| *E. coli* S17-1 | B - 15483 |

Other vectors, such as pSUP102 or pSUP205, are known from the literature and are obtained from known vectors according to analogous methods (Simon et al., Methods of Enzymology 118, 640 ff (1986) and Biotechnology, November 1982)1. The construction of mobilizable vectors is likewise described in European patent application No. 89 130 473.7 EP-A-0375 889.

In order to test the transposon activity, the ~14.4 kb fragment of the R plasmid is inserted into a mobilizable vector and this construct is introduced via conjugation into a coryneform bacterium, especially into one which produces amino acids. A *Corynebacterium glutamicum* is selected with preference.

In a further embodiment, the present invention relates to a method for the mutagenesis of a gram-positive bacterium comprising introducing the transposon according to claim 1 or 2 with the aid of a carrier plasmid by means of transformation into the bacterium wherein the carrier plasmid does not replicate in the bacterium or only replicates at low incubation temperatures. The transposon is introduced into the recipient with the aid of a suitable carrier plasmid either by means of transformation or conjugation. The test vectors constructed using the named *E. coli* vectors and containing the transposon are transferred by means of conjugation from *E. coli* mobilizer strains into the gram-positive bacteria according to a method like that described in European patent application No. 89 120 473.7 (corresponds to German patent application P 38 41 453.8).

In another embodiment, the present invention relates to a method for the mutagenesis of a gram-positive bacterium comprising conjugative transfer of mobilizable vectors from *E. coli* mobilizer strains wherein restriction-defective cells of the gram-positive bacterium are produced and are crossed with an *E. coli* strain carrying the mobilizable vector described above.

Restriction-defective cells of a gram-positive bacteria are produced thereby and are mixed in accordance with known crossing methods with an *E. coli* mobilizer strain carrying the mobilizable test vector. While the donor is preferably in the logarithmic growth phase, the stationary growth phase has proved to be advantageous for the state of the recipient. Donor cells and recipient cells are generally used in a ratio of 1:1 to 1:10, preferably 1:1 to 1:6.

The restriction defect can be genetically brought about and generated e.g. by means of mutagenic agents (e.g. NTG: methylnitronitrosoguanidine); however, it can also be brought about physiologically, e.g. by means of a heat shock. A heat treatment of the recipient immediately before the crossing has proved to be especially effective. Intact or spheroplasted cells are to be used thereby. A heat shock for a period of 1 to 30 min., preferably approximately 9 min., at 45° to 55° C., preferably approximately 49° C., makes it possible with the following increase of the transfer frequency to solve the problem of the invention.

In a further embodiment, the present invention relates to a gram-positive bacterium (preferably, a coryneform bacterium) wherein the bacterium is transformed with the mobilizable, non-self-transferrable vector (test vector) described above. In one preferred embodiment, the bacterium contains an auxotrophy generated by the transformation.

The test vector of the invention which does not replicate in this bacterium is largely lost in the recipient cell and with it the inserted DNA fragment of the R plasmid.

It was found for the first time that a transposon test vector integrates into the chromosome of a coryneform bacterium functioning as recipient to a considerable extent and that the integration of a certain DNA segment of the R plasmid DNA into the chromosome of the recipient occurs (transposition). The integrations take place at different positions of the chromosome.

An investigation of the integration mutants obtained using the test vector pK1 (FIG. 3) shows that the vector pK1 integrates non-specifically after the mobilization of *E. coli* into the chromosome of the strain *C. glutamicum* ATCC13032 selected as recipient. *C. glutamicum* cells with three different auxotrophies (A1 Leu⁻ (leucine auxotropy), AZ Trp⁻ (tryptophan auxotrophy), A3 Ser⁻ (serine auxotrophy)) were found in the transposon mutagenesis batches carried out. A prerequisite for such occurrences is the presence of a transposon and of an insertion element on the test vector. The DNA segment essential for this integration is on the DNA fragment of the R plasmid pCxM82B, which is a component of this test vector.

The present invention is described in further detail in the following non-limiting examples.

EXAMPLE 1

Figure 2B:
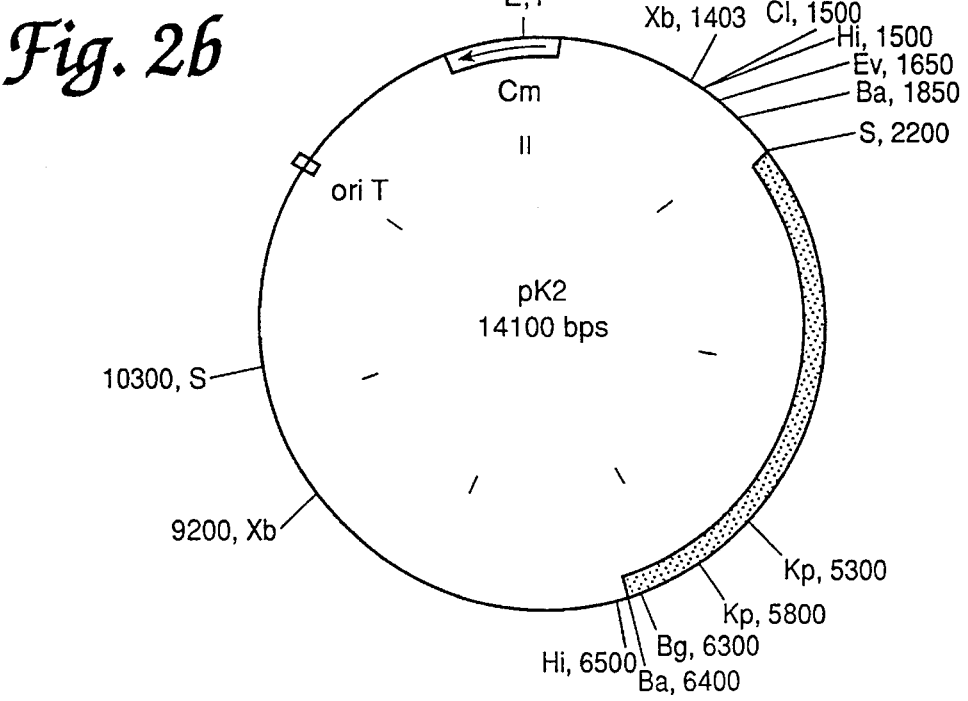
Figure 3B:
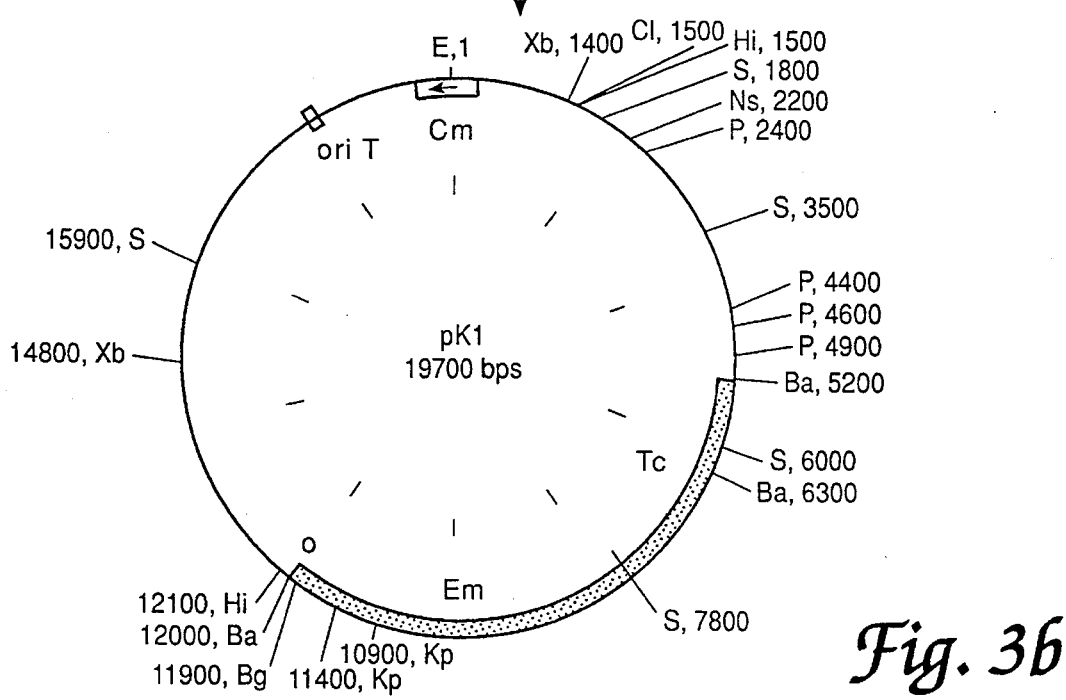

Construction of the Transposon Test Vector pK1
(FIGS. 2 and 3)

The mobilizable *E. coli* vector pSUP102 (Simon et al. (1983) Biotechnology 1, Methods in Enzymology, 118, 641–659) was linearized with the enzyme SalI. The *E. coli* vector pSAl E2 (*E. coli* vector pUC19 (Norrander et al. (1983) Gene 26, 101ff) with the R plasmid fragment SalE2) was pretreated in the same manner. The cleavage batches were mixed and subsequently ligated. *E. coli* S17-1 (Simon et al. (1983) Biotechnology 1, Methods in Enzymology, 118, 641–659) was then transformed with this mixture. A plasmid was able to be isolated from the transformants which imparts resistance to 50 µg/ml chloramphenicol (cm) and 30 µg/ml erythromycin (Em) on agar plates of the antibiotic medium No. 3 of the Oxoid company. This plasmid, named pK2, consists of the vector pSUP102 and the 8.1 kb R plasmid fragment SalE2. The plasmid pK2 was linearized with HindIII and subsequently religated. The ligation mixture was transformed into *E. coli* S17-1. The plasmid pK2ΔHi (vector pK2 with the HindIII fragment deleted) was able to be isolated from the transformants. Plasmid pK2ΔHi was linearized with HindIII and mixed with the vector p2Hi4 (plasmid PUC19 with the R plasmid fragment 2Hi4) treated in the same manner and ligated. *E. coli* S17-1 was transformed with the ligation mixture. The Plasmid pK1 (FIG. 3) was able to be isolated from the transformants. This plasmid consists of a part of the *E. coli* vector pSUP102 and the ~14.4 kb fragment of the R plasmid pCxM82B and exhibits a total length of ~19.7 kb.

EXAMPLE 2

Performance of Transposon Mutagenesis With the Plasmid pK1 for Generating Auxotrophic *C. glutamicum* Cells The donor *E. coli* S17-1/pK1 is cultivated 20 h in 10 ml LBGEm$_{50}$ (Luria broth with 1 g/l glucose, 50 µg Erythromycin per milliliter of culture medium) (Maniatis et al. (1982) Molecular Cloning, Cold Spring HArbor Lab) (initial culture).

The recipient *C. glutamicum* ATCC 13032 is cultivated overnight in 100 ml LBG up to an optical density$_{580}$ =4.0. 100 ml LBGEm$_{50}$ are inoculated with 1 ml of the initial donor culture and cultivated to an optical density$_{580}$=1.0. 15 ml of the recipient culture are incubated for 9 min. at 49° C. Donor culture and recipient culture are centrifuged off separately and washed.

After the resuspension, donor cells and recipient cells are mixed in a ratio of 1:1. The crossing mixture (in the optimum volume of 0.2 ml) is dripped onto NC filters (nitrocellulose filters of the Sartorius company) which were previously placed on LBGEm$_{0.2}$ agar plates. The crossing mixture is incubated approximately 20 h at 37° C. in an incubator. After the incubation, the selection of the crossing mixture on LBGNx$_{50}$(50 µg nalidixic acid per milliliter culture medium) Em$_{25}$(25 µg erythromycin per milliliter culture medium) takes place. After 2 days incubation of the plates at 30° C., the erythromycin-resistant colonies can be transferred onto LBGEm$_{50}$.MMEm$_{50}$ (MM= minimal medium, Ebbinghausen et al. (1989) Arch. Microbiol. 151, 238ff) LBGTc$_{10}$ and LBGGm$_{10}$.

EXAMPLE 3

Analysis of Mutants

99% of the integration mutants are resistant to Em, Tc and Cm (resistance genes of the vector pK1; Em' and Tc' are resistance genes of the R plasmid pCxM82B; Cm' is a resistance gene of the vector pSUP102); the vector pK1 is integrated into the chromosome in these transconjugants. Only a resistance to erythromycin can be determined in 1% of the transconjugants (a partial range of the R plasmid DNA is integrated here into the chromosome; the Em resistance gene is located in this DNA range of the R plasmid pCxM82B). The non-specific integration of the vector pK1 or of a part of the vector into the chromosome of *C. glutamicum* was able to be demonstrated by means of the hybridization of chromosomal DNA from insertants with digoxygenine-dUTP-labeled R plasmid DNA. The DNA labeling was carried out with the "DNA Labeling and Detection Kit" of Boehringer Mannheim. The performance took place according to the instructions of the manufacturer. The DNA transfer took place according to the method of Southern (1975) J. Mol. Biol. 98, 503ff.

Approximately 130–150 transconjugants are obtained per crossing batch under the above-named conditions. Auxotrophic cells are found with a frequency of 0.5% to 1% among these transconjugants.

Three auxotropic *C. glutamicum* cells (A1 Leu⁻, A2 Trp⁻, A3 Ser⁻) were isolated in the previously performed transposon mutagenesis batches. These cells do not grow on MMEm$_{50}$. These cells were supplemented according to the method of Holliday (1956) Nature 4540, 987 in order to determine the auxotrophy.

It was determined that the vector pK1 integrates non-specifically into the chromosome of *C. glutamicum* after mobilization of *E. coli* to *C. glutamicum*. This non-specific integration of the R plasmid fragment into the chromosome was demonstrated by means of hybridization of the entire DNA of the insertants with labeled R plasmid DNA. The ability of non-specific integration is associated with the presence of the ~14.4 kb R plasmid fragment and is explained by the presence of a transposon or of an insertion element.

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

Figure 1:
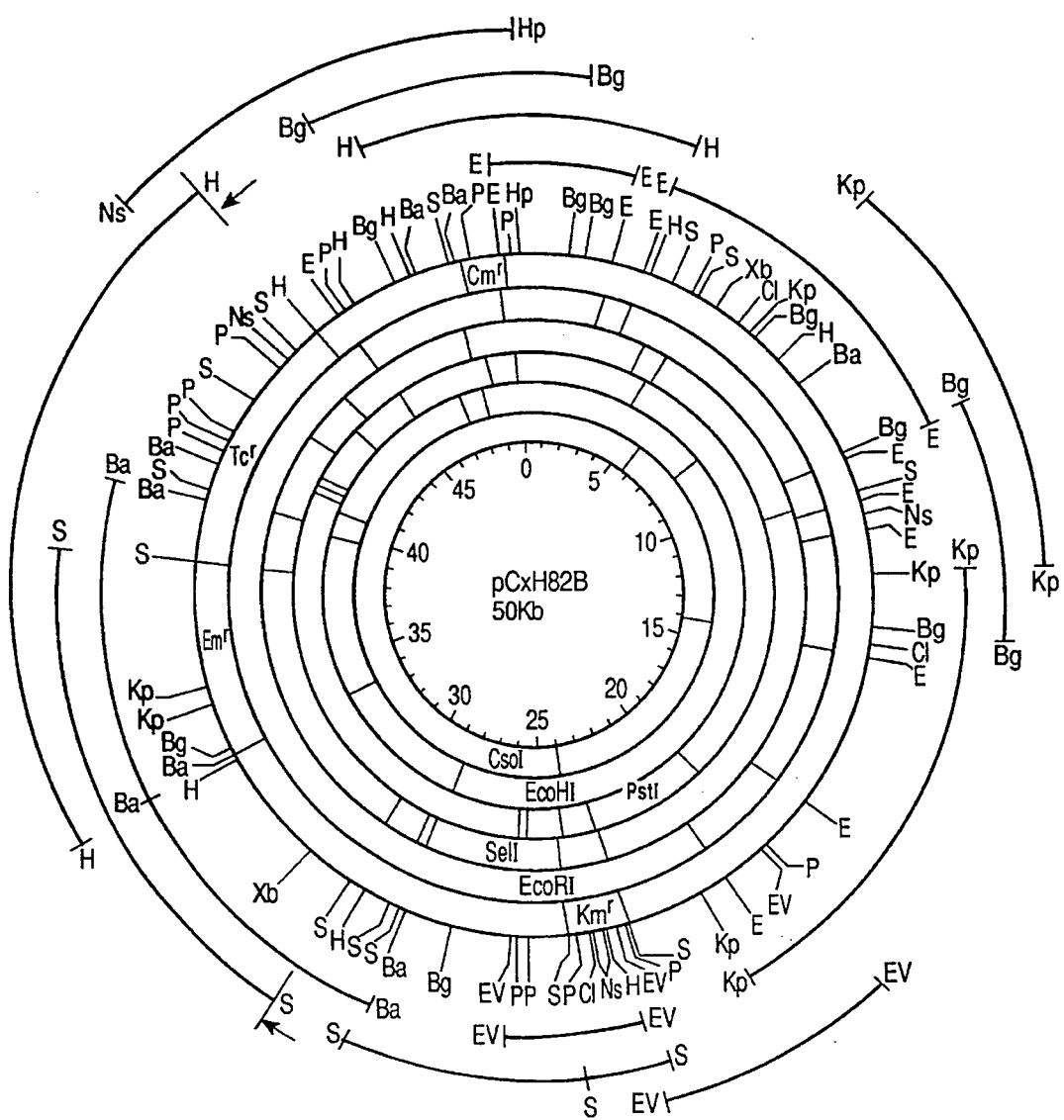
FIG. 1. The circular restriction map of the R plasmid pCxM82B. Abbreviations used in the figure include: Ba, BamHI; Bg, BglII; Cl, ClaI; E, EcoRI; EV, EcoRV; H, HindIII; Kp, KpnI; Ns, NsiI; P, PstI; S, SalI; Xb, XbaI; Hp, HpaI. Additional features of the fragment claimed are also shown.

What is claimed is:

1. A transposon consisting of a DNA segment of the R plasmid pCxM82B wherein said DNA segment comprises:

(a) a segment of DNA necessary for integration;

(b) a segment of DNA coding for tetracycline resistance, and (c) a segment of DNA coding for erythromycin resistance, wherein said DNA segment of the R plasmid pCxM82B comprises an approximately 14.4 kb DNA segment delimited by a SalI cleavage site (coordinate 30.4 kb) and a HindIII cleavage site (coordinate 44.8 kb) of pCxM28B set forth in FIG. 1.

2. A mobilizable, non-self-transferrable vector (test vector) comprising:

a) a mobilizable, non-self-transferrable *E. coli* vector comprising a DNA segment containing a replicon functional in *E. coli* and a second DNA segment containing DNA segments coding for the mobilization and transfer functions (Mob site and ori T), and b) the transposon according to claim 1.

3. The mobilizable, non-self-transferrable vector (test vector) according to claim 2, wherein said mobilizable, non-self-transferrable *E. coli* vector contains a 1.9 kb DNA fragment (mob site) of the plasmid RP4.

4. The mobilizable, non-self-transferrable vector (test vector) according to claim 2, wherein said mobilizable, non-self-transferrable *E. coli* vector is pSUP101, pSUP102, pSUP201, pSUP202, pSUP203, pSUP205, pSUP301, or pSUP401.

5. The mobilizable, non-self-transferrable vector (test vector) according to claim 2, wherein said test vector is pK1 set forth in FIG. 3.

6. A method for the mutagenesis of a coryneform bacterium comprising conjugative transfer of mobilizable vectors from *E. coli* mobilizer strains wherein restriction-defective cells of the gram-positive bacterium are produced and are crossed with an *E. coli* strain carrying the mobilizable vector in which the transposon according to claim 1 is contained.

7. The method according to claim 6, wherein said mobilizable vector is pK1 set forth in FIG. 3.

8. A coryneform bacterium wherein said bacterium is transformed with the mobilizable, non-self-transferrable vector (test vector) according to claim 2.

9. The bacterium according to claim 8, wherein said bacterium is transformed by the test vector pK1.

10. The bacterium according to claim 9, wherein said bacterium contains an auxotrophy generated by said transformation.

11. The bacterium according to claim 8, wherein said bacterium is *Corynebacterium glutamicum*.

12. The bacterium according to claim 11, wherein said bacterium is transformed by the test vector pK1.

13. The bacterium according to claim 12, wherein said bacterium contains an auxotrophy generated by said transformation.

\* \* \* \* \*